United States Patent
Acar et al.

(10) Patent No.: US 12,270,589 B2
(45) Date of Patent: Apr. 8, 2025

(54) ANTIMICROBIAL AIR DUCTS

(71) Applicant: Whirlpool Corporation, Benton Harbor, MI (US)

(72) Inventors: Mehmet Ali Acar, Izmir (TR); Muhammad Khizar, St. Joseph, MI (US); Andrea Olivani, Milan (IT); Matteo Parnisari, Biandronno (IT)

(73) Assignee: Whirlpool Corporation, Benton Harbor, MI (US)

( * ) Notice: Subject to any disclaimer, the term of this patent is extended or adjusted under 35 U.S.C. 154(b) by 840 days.

(21) Appl. No.: 16/115,817

(22) Filed: Aug. 29, 2018

(65) Prior Publication Data

US 2020/0072527 A1  Mar. 5, 2020

(51) Int. Cl.
*F25D 17/04* (2006.01)
*A61L 9/20* (2006.01)
(Continued)

(52) U.S. Cl.
CPC ............ *F25D 17/042* (2013.01); *A61L 9/205* (2013.01); *B01D 53/007* (2013.01);
(Continued)

(58) Field of Classification Search
CPC ...... F25D 17/042; F25D 17/065; F25D 17/08; F25D 2317/041; F25D 2317/0417; F25D 17/067; A61L 9/205; A61L 2209/12; B01D 53/007; B01D 53/885; B01D 2255/104; B01D 2255/20707; B01D 2255/20715; B01D 2255/209; B01D 2255/802; B01D 2257/708; B01D 2257/91; B01J 23/08;
(Continued)

(56) References Cited

U.S. PATENT DOCUMENTS

| | | | |
|---|---|---|---|
| 4,909,040 A | 3/1990 | Fletrin | |
| 5,919,422 A * | 7/1999 | Yamanaka | A61L 2/232 422/121 |

(Continued)

FOREIGN PATENT DOCUMENTS

| | | | |
|---|---|---|---|
| CN | 103623452 A | 3/2014 | |
| CN | 203824216 U * | 9/2014 | F25D 23/12 |

(Continued)

OTHER PUBLICATIONS

CN206989575U English translation (Year: 2018).*
(Continued)

*Primary Examiner* — Regina M Yoo
(74) *Attorney, Agent, or Firm* — Price Heneveld LLP

(57) ABSTRACT

A refrigerator includes a cabinet coupled to one or more doors forming a storage compartment and an air purifying duct system positioned in the storage compartment. The air purifying duct system includes an air duct in fluid communication with the storage compartment; a fan configured to circulate air between the storage compartment and air duct; a photocatalyst disposed on a portion of the interior surface; one or more LEDs positioned to project light across the air duct and onto the photocatalyst; and an air circulation path configured to direct pathogens within the storage compartment into the air duct using the fan and circulate purified air into the storage compartment.

23 Claims, 11 Drawing Sheets

(51) Int. Cl.
| | |
|---|---|
| *B01D 53/00* | (2006.01) |
| *B01D 53/88* | (2006.01) |
| *B01J 23/08* | (2006.01) |
| *B01J 23/50* | (2006.01) |
| *B01J 23/66* | (2006.01) |
| *B01J 35/23* | (2024.01) |
| *B01J 35/39* | (2024.01) |
| *F25D 17/06* | (2006.01) |
| *F25D 17/08* | (2006.01) |
| *F24F 8/24* | (2021.01) |

(52) U.S. Cl.
CPC ............ *B01D 53/885* (2013.01); *B01J 23/08* (2013.01); *B01J 23/50* (2013.01); *B01J 23/66* (2013.01); *B01J 35/23* (2024.01); *B01J 35/39* (2024.01); *F25D 17/065* (2013.01); *F25D 17/08* (2013.01); *A61L 2209/12* (2013.01); *B01D 2255/104* (2013.01); *B01D 2255/20707* (2013.01); *B01D 2255/20715* (2013.01); *B01D 2255/209* (2013.01); *B01D 2255/802* (2013.01); *B01D 2257/708* (2013.01); *B01D 2257/91* (2013.01); *F24F 8/24* (2021.01); *F25D 2317/041* (2013.01); *F25D 2317/0417* (2013.01)

(58) Field of Classification Search
CPC ........ B01J 23/50; B01J 23/66; B01J 35/0013; B01J 35/004; F24F 2003/1675; A01N 25/28; A01N 55/02
See application file for complete search history.

(56) References Cited

U.S. PATENT DOCUMENTS

| | | | |
|---|---|---|---|
| 5,933,702 A * | 8/1999 | Goswami | ................ A61L 9/205 422/186.3 |
| 6,606,869 B2 | 8/2003 | Takahashi et al. | |
| 6,736,885 B2 * | 5/2004 | Kaiser | ................ B01D 46/0023 55/385.3 |
| 6,797,044 B2 | 9/2004 | Ou Yang et al. | |
| 7,063,820 B2 * | 6/2006 | Goswami | ................ A61L 2/02 422/186.3 |
| 9,803,909 B2 | 10/2017 | Son et al. | |
| 9,803,910 B2 | 10/2017 | Kim et al. | |
| 9,903,634 B2 | 2/2018 | Son et al. | |
| 10,712,084 B2 * | 7/2020 | Choi | ........................ A61L 2/084 |
| 2003/0024254 A1 * | 2/2003 | Yoshida | ................ F25D 17/065 62/78 |
| 2005/0268623 A1 | 12/2005 | Urakubo et al. | |
| 2007/0193875 A1 | 8/2007 | Ham et al. | |
| 2007/0266725 A1 | 11/2007 | Anikhindi et al. | |
| 2008/0274018 A1 | 11/2008 | Kawai et al. | |
| 2008/0286643 A1 * | 11/2008 | Iwasaki | ................ H01G 9/2013 429/111 |
| 2009/0098014 A1 * | 4/2009 | Longstaff | .............. F24F 1/0071 422/4 |
| 2009/0123343 A1 | 5/2009 | Kwiatkowski | |
| 2009/0136389 A1 * | 5/2009 | Park | ..................... B01D 53/007 422/122 |
| 2013/0104579 A1 | 5/2013 | Zhou | |
| 2014/0360213 A1 | 12/2014 | Son et al. | |
| 2015/0033784 A1 | 2/2015 | Park et al. | |
| 2015/0064069 A1 | 3/2015 | Yi et al. | |
| 2015/0238644 A1 * | 8/2015 | Sung | ..................... B01J 35/004 422/187 |
| 2016/0047587 A1 * | 2/2016 | Sasaki | .................. H04N 5/2252 239/71 |
| 2017/0246333 A1 | 8/2017 | Carbone et al. | |
| 2017/0307280 A1 | 10/2017 | Schmidt et al. | |
| 2018/0099062 A1 | 4/2018 | Campalans et al. | |
| 2018/0238613 A1 * | 8/2018 | Choi | ....................... A61L 9/205 |

FOREIGN PATENT DOCUMENTS

| | | | | |
|---|---|---|---|---|
| CN | 204219436 U | * | 3/2015 | ............... A61L 2/20 |
| CN | 206989575 U | * | 2/2018 | ............ F25D 23/10 |
| EP | 2527769 A2 | | 11/2012 | |
| JP | 2000279493 A | | 10/2000 | |

OTHER PUBLICATIONS

CN203824216U English translation (Year: 2014).*
CN204219436U English translation (Year: 2015).*
Vilas S. Desai, Antimicrobial Activity of Titanium Dioxide nanoparticles Synthesized by Sol-Gel Technique—Science Alert, Research Journal of Microbiology, 2009, pp. 97-103, vol. 4(3).
Abdel-Fatah Wafa I et al., Role of silver nanoparticles in imparting antimicrobial activity of titanium dioxide, Materials Letters, Elsevier, May 9, 2016, pp. 190-193, vol. 179.
Juliane Maria Guerreiro-Tanomaru et al., Effect of Zirconium Oxide and Zinc Oxide Nanoparticles on Physicochemical Properties and Antibiofilm Activity of a Calcium Silicate-Based material, The Scientific World Journal, vol. 2014, Nov. 6, 2014, pp. 1-6.
A. Cochis, Data in support of Gallium (Ga3+) antibacterial activities to counteract *E. coli* and *S. epidermidis* biofilm formation onto pro-osteointegrative titanium surfaces, Science Direct, Data in Brief, vol. 6, Jan. 22, 2016, pp. 758-762.

* cited by examiner

ANTIMICROBIAL AIR DUCTS

FIELD OF THE INVENTION

The present device generally relates to antimicrobial air ducts for use in a refrigerator, and more specifically, to air ducts having one or more active surfaces used to remove particulate matter, kill microbes, and decompose volatile organic compounds in a refrigerator.

BACKGROUND OF THE INVENTION

With the latest development of extra-large capacity refrigerators, there has been an emerging demand for highly robust antimicrobial technology such as air disinfection systems for food preservation and related features. Such systems are used to avoid the spoilage of food and produce stored in refrigerators for extended periods. Due to the unavailability of adequate antimicrobial technology, huge amounts of food, including produce, can go wasted even when stored in adequately low temperature refrigerators. Moreover, because of the increasing cost of commodities and food product costs, consumers are demanding efficient food storage technology for its longevity without compromise to its freshness.

One food preservation technique currently being used includes titanium dioxide ($TiO_2$) charged using a mercury lamp lighting system but due to the harmful effects of the mercury lamp integrated in this system, it could not meet the specifications or expectations for an antimicrobial application. In addition, the use of mercury in these types of UV lamp systems could be extremely dangerous due to health hazards and other handling issues associated with mercury. Another preservation and antimicrobial technique frequently used includes ozonizer systems that are directly integrated into the refrigerator. However, with time, significant decline in ozonizer performance is reported and their high cost makes these applications prohibitively expensive. Nano-misting techniques have also been studied but due to the harmful nature of the zinc and silver used in the applied nano-particles; these materials also did not meet consumer market requirements.

Accordingly, the need for an efficient and affordable antimicrobial filtration system is required in the market place for consumers to better accommodate food safety and longer storage times for valuable foodstuffs.

SUMMARY OF THE DISCLOSURE

According to one aspect of the present disclosure, a refrigerator is provided. The refrigerator includes a cabinet coupled to one or more doors forming a storage compartment and an air purifying duct system positioned in the storage compartment. The air purifying duct system includes an air duct in fluid communication with the storage compartment; a fan configured to circulate air between the storage compartment and air duct; a photocatalyst disposed on a portion of the interior surface; one or more LEDs positioned to project light across the air duct and onto the photocatalyst; and an air circulation path configured to direct pathogens within the storage compartment into the air duct using the fan.

According to another aspect of the present disclosure, a refrigerator is provided. The refrigerator includes a cabinet coupled to one or more doors forming a storage compartment; an air duct in fluid communication with the storage compartment; a fan configured to circulate air between the storage compartment and air duct; a nano-coating disposed on a portion of an interior surface of the air duct; and an air circulation path configured to direct pathogens within the storage compartment into the air duct using the fan.

According to yet another aspect of the present disclosure, an air purifying duct system is provided. The air purifying duct system includes an air duct in fluid communication with a storage compartment; a fan configured to circulate air between the storage compartment and air duct; a nano-coating including titanium dioxide ($TiO_2$), silver (Ag), zirconium dioxide ($ZrO_2$), and/or gallium (Ga); and an air circulation path configured to direct pathogens within the storage compartment into the air duct using the fan and circulate purified air into the storage compartment. In some aspects, the air purifying duct system may additionally include a photocatalyst disposed on a portion of the interior surface and one or more LEDs positioned to project light across the air duct and onto the photocatalyst. In some aspects, the nano-coating may include titanium dioxide ($TiO_2$) and silver (Ag) or the nano-coating may include zirconium dioxide ($ZrO_2$) and gallium (Ga).

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

Figure 1A:
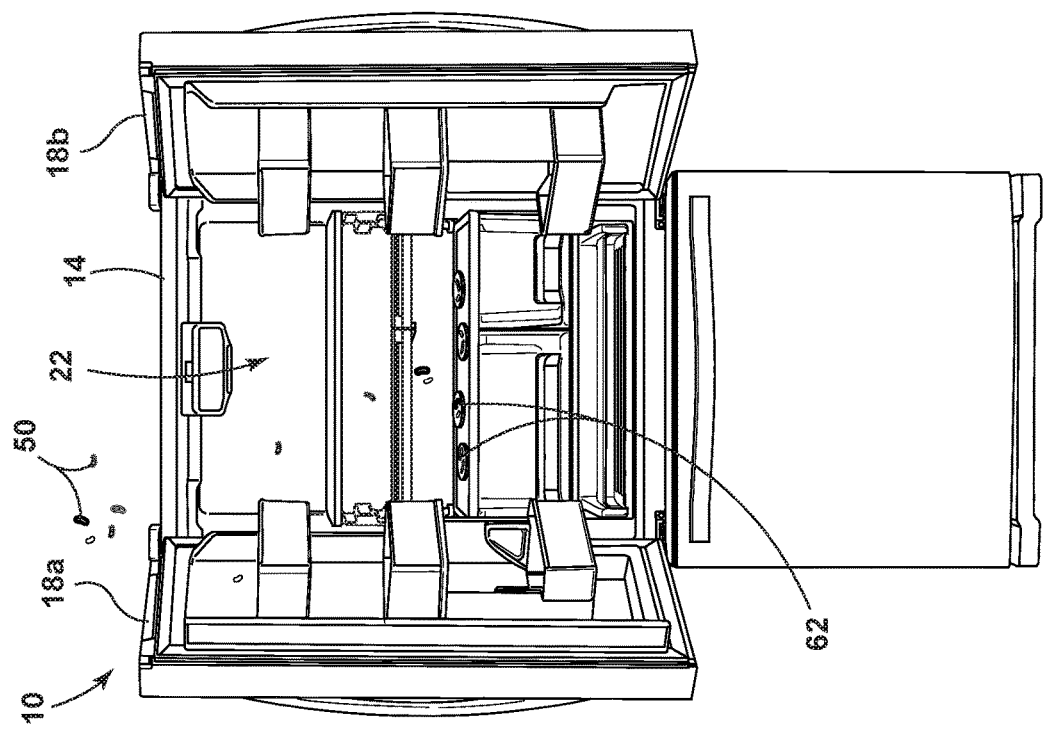
FIG. 1A is a front isometric view of a refrigerator having bacteria contaminated food.

For purposes of description herein the terms "upper," "lower," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Referring to FIGS. 1D-5B, the reference numeral 10 refers to a refrigerator. The refrigerator 10 includes a cabinet 14 coupled to one or more doors 18 forming a storage compartment 22 and an air purifying duct system 24 positioned in the storage compartment 22. The air purifying duct system 24 includes an air duct 26 in fluid communication with the storage compartment 22; a fan 30 coupled to an interior surface 34 of the air duct 26 wherein the fan 30 is configured to circulate air between the storage compartment 22 and air duct 26; a photocatalyst 38 disposed on a portion of the interior surface 34; one or more LEDs 42 positioned to project light across the air duct 26 and onto the photocatalyst 38; and an air circulation path 46 configured to direct pathogens, particulate matter, and/or airborne bacteria 50 within the storage compartment 22 into the air duct 26 using the fan 30 and circulate purified air into the storage compartment 22.

The air purifying duct system 24 provides an antimicrobial technology for in-vitro time-dependent reduction of microbial populations after exposure to a nano-coating 54 and/or the photocatalyst 38 being exposed to UV and/or visible light from the LEDs 42. The coating and purification technology incorporated into this air purifying duct system 24 includes the nano-coating 54, photocatalyst 38, and/or LEDs 42 where each respective component can provide an efficient air treatment capability that may interact with the deoxyribonucleic acid (DNA) and/or trigger a cascade of other biological reactions in harmful bacteria responsible for the spoilage of food stored at low temperatures in refrigerators. In some aspects, the photocatalyst 38 may include a photocatalytic nanostructured titanium dioxide ($TiO_2$) film, coating, or membrane deposited using sol-gel. In other aspects, the nano-coating 54 may include a nanostructured film, coating, or membrane deposited using sol-gel. The sol-gel can be doped to impart the titanium dioxide ($TiO_2$) or other metal/metal oxide mixture as the photocatalyst 38 that may be activated using visible light and/or an ultraviolet wavelength less than 700 nanometers (e.g., 245-700 nanometer wavelengths and 375-380 nanometer wavelengths) using a 12 volt UV LED strip or panel 82 (see FIG. 4) is provided. In some aspects, the photocatalyst 38 may be activated using an ultraviolet wavelength less than about 400 nm and/or visible light ranging from about 400 nm to about 700 nm.

Referring now to FIGS. 1A-1D, a variety of different refrigerator environments were studied to determine how bacteria and other particulate matter may be introduced into the storage compartment 22 of the refrigerator 10. Each of the refrigerators 10 is shown having the cabinet 14 with the storage compartment 22 enclosed by the cabinet 14 and the door 18, in particular, a first door 18a and a second door 18b. In the first test environment illustrated in FIG. 1A, the introduction of bacterial contamination to the storage compartment 22 was accomplished by positioning a contaminated chicken breast 58 containing many different types of bacteria. The test environment provided in FIG. 1A demonstrated that the bacteria growing on the contaminated chicken breast 58 did not spread to or reach any of plurality of petri dishes 62 proving that refrigerator bacterial contamination is likely not due to food cross-contamination, except for direct food contact.

Figure 1B:
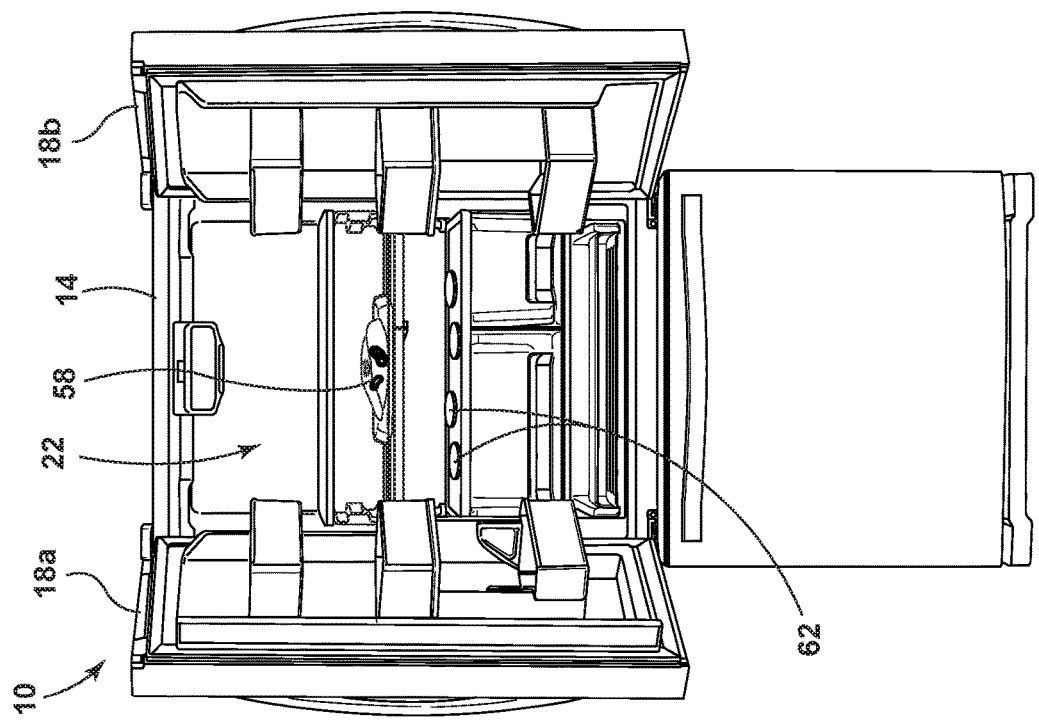
FIG. 1B is a front isometric view of a refrigerator having no food.

In the second test environment illustrated in FIG. 1B, the introduction of bacterial contamination to the storage compartment 22 was accomplished by circulating air from outside the refrigerator 10 by opening and closing the first and second refrigerator doors 18a, 18b. By opening and closing the refrigerator doors 18a, 18b, airborne bacteria 50 was introduced to the storage compartment 22 and was able to contact and grow in the petri dishes 62. The refrigerator 10 in FIG. 1B did not include any air purifying or circulation system. The test environment provided in FIG. 1B demonstrates that bacteria introduced into the refrigerator 10 and corresponding foodstuffs is likely determined by the introduction of airborne bacteria 50 during refrigerator door 18 opening and closing.

Figure 1D:
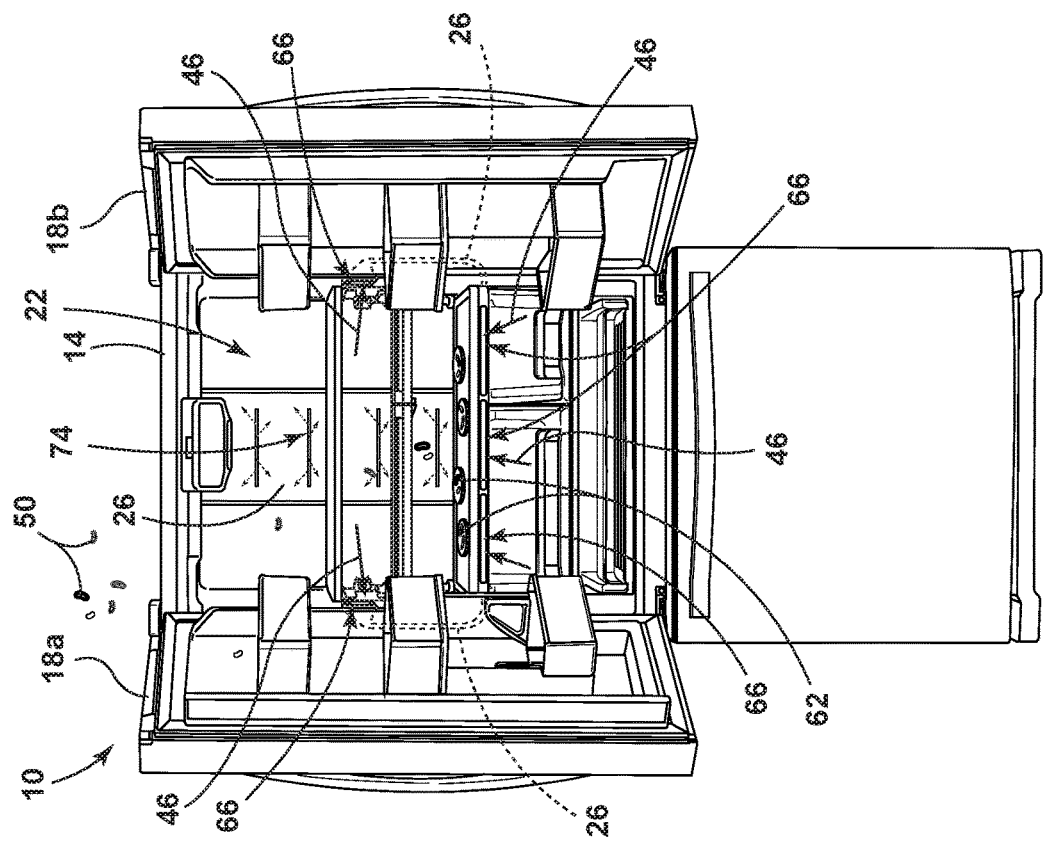
FIG. 1D is a front isometric view of a refrigerator having an air purifying duct system according to some aspects of the disclosure.
Figure 1C:
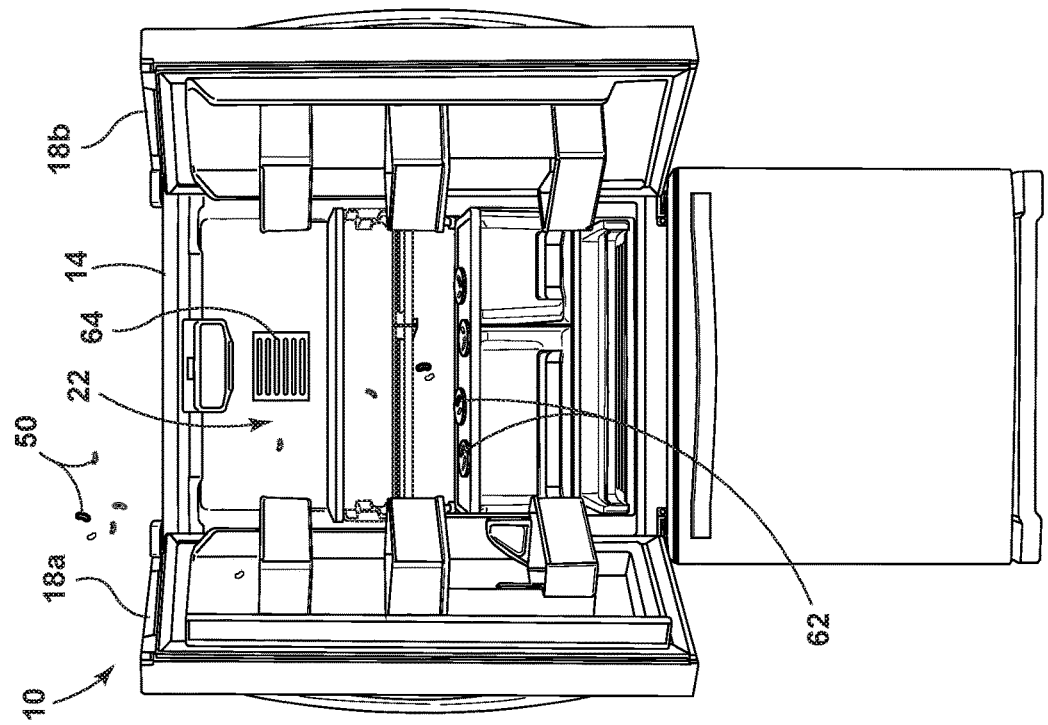
FIG. 1C is a front isometric view of a refrigerator having a standard circulation fan.

In the third test environment illustrated in FIG. 1C, the introduction of bacterial contamination to the storage compartment 22 was accomplished as described in FIG. 1B, by opening and closing the refrigerator doors 18a, 18b. The additional variable introduced in FIG. 1C includes a standard fan driven circulation system 64 using only a single fan assembly which is currently implemented in many refrigerators. The test environment provided in FIG. 1C demonstrated that the single fan circulation system had minimal to no noticeable effect on the airborne bacteria 50 introduced into the storage compartment 22 of the refrigerator 10.

In the fourth test environment illustrated in FIG. 1D, a front isometric view of the refrigerator 10 having the air purifying duct assembly 192 (see FIG. 9B) according to some aspects of the disclosure is provided. The introduction of bacterial contamination to the storage compartment 22 was accomplished as described in FIGS. 1B and 1C, by opening and closing the refrigerator doors 18a, 18b. The refrigerator 10 in FIG. 1D additionally includes the air purifying duct assembly 24 equipped with the air duct 26, fan 30, and photocatalyst 38 where the photocatalyst 38 can be activated by at least one LED 42 (see FIG. 3). In some aspects, the photocatalyst 38 can be activated by an array of LEDs 42 and/or a plurality of LEDs 42. The test environment provided in FIG. 1D demonstrated that the combination of the air purifying system 24 using the photocatalyst 38 and/or nano-coating 54 are able to reduce bacterial contamination in the storage compartment 22.

The coatings 78 (see FIGS. 3A and 3B) used in the air purifying duct system 24 may be formed using the photocatalyst 38 and/or the nano-coating 54. The photocatalyst 38 and the nano-coating 54 may be distinguished from each other based on the use and/or need of LED 42 activation. As used herein, the term "photocatalyst 38" is defined to include, but is not limited to, metals, metal oxides, metal blends, metal oxide blends, and/or metal and metal oxide blends that have one or more band gap energies that match or correspond to the photons emitted from the LEDs 42. As used herein, the term "nano-coating 54" is defined to include an antimicrobial surface including, but not limited to, metals, metal oxides, metal blends, metal oxide blends, and/or metal and metal oxide blends that inhibit, damage, and/or kill microorganisms including bacteria without the need or use of selected wavelengths of LED lighting. In some aspects, certain materials described herein and used in the coatings 78 may be considered both a photocatalyst 38 and/or a nano-coating 54.

Still referring to FIG. 1D, one or more duct intakes 66 may direct polluted air into the air ducts 26 of the air purifying duct system 24 (see FIG. 2) to be purified. In some aspects, the one or more duct intakes 66 may be positioned on opposing cabinet walls, proximate an outer edge portion of the cabinet 14, proximate a shelf, or a combination thereof. As discussed in FIG. 1B, the opening and closing of refrigerator doors 18a, 18b, can introduce airborne bacteria 50 and other related pathogens into the storage compartment 22 in high enough concentrations to be able to contact and grow in petri dishes 62. The term "pathogens" as used herein, is defined to include airborne bacteria 50, viruses, fungi, and/or molds. In some aspects, the introduction and application of the air purifying duct system 24, including one or more light activated photocatalysts 38 (see FIG. 3) coupled to at least one duct wall 70 where the photocatalyst 38 can be activated using the plurality of LEDs 42, are able to reduce bacterial contamination in the storage compartment 22 by up to 70% when compared to the environments provided in FIGS. 1B and 1C. The circulated air of the air circulation path 46 exits the air ducts 26 of the air purifying duct system 24 through one or more duct exhausts 74 positioned in the storage compartment 22.

Figure 2A:
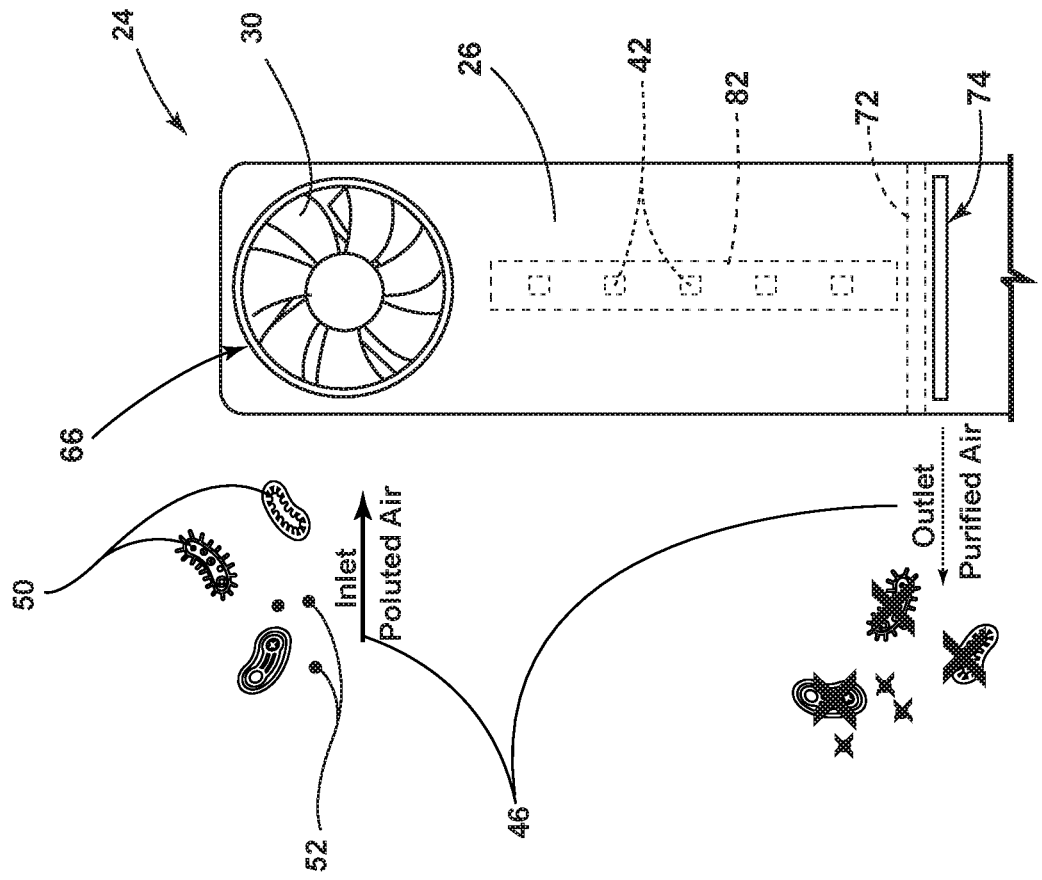
FIG. 2A is an isolated isometric view of the air purifying duct system provided in FIG. 1D according to some aspects of the disclosure.

Referring now to FIG. 2A, an isolated isometric view of the air purifying duct system 24 according to some aspects of the disclosure is illustrated. The air circulation path 46 is directed into the air purifying duct system 24 through one or more duct intakes 66 by passing through a grate 66 and/or filter 72. As the air circulation path 46 passes through the duct intakes 66, the air continues through one or more air ducts 26 that may vary in numbers, shape, and positioning as determined by the design and application of the refrigerator 10. Bacterial contamination present in the circulated air of air circulation path 46 may be reduced or at least partially eliminated using the nano-coating 54 and/or photocatalyst 54 where the photocatalyst 54 may be activated using selected wavelengths projected by LEDs 42. The nano-coating 54 and/or photocatalyst 38 may be positioned and/or coupled to one or more duct walls 70 (see FIG. 3) of the air ducts 26. The circulated air of air circulation path 46 exits the air ducts 26 of the air purifying duct system 24 through one or more air duct exhausts 74 positioned in the storage compartment 22. In some aspects, the air purifying duct system 24 includes the nano-coating 54 but does not include the photocatalyst 38. In other aspects, the air purifying duct system 24 includes the photocatalyst 38 but does not include the nano-coating 54. In still other aspects, the air purifying duct system 24 includes both the nano-coating 54 and the photocatalyst 38.

Still referring to FIG. 2A, the air duct intakes 66 of the air purifying duct system 24 may be positioned on opposing walls of the cabinet 14 in some aspects of the present disclosure. In other aspects, the air duct intakes 66 may be additionally or alternatively positioned against or in proximity to one or more refrigerator shelves to direct the air circulation path 46. In some aspects, the air purifying duct system 24 may be positioned flush with the one or more cabinet walls and/or refrigerator doors 18a, 18b (see FIG. 1D). In other aspects, the air purifying duct system 24 may be positioned to stick out from the one or more cabinet walls and/or refrigerator doors 18a, 18b to form a ledge or protrusion. In other aspects, the cabinet 14 may be cutout or formed with an indentation to receive the air duct intakes 66 to form an even or flat surface on the cabinet walls. In some aspects, at least one air duct intake 66 is positioned in opposing cabinet walls. In other aspects, the one or more air duct intakes 66 may be positioned on a front lip or edge of the cabinet 14 configured to direct the air circulation path 46 (see FIG. 1D) and corresponding fresh outside air into the air purifying duct system 24 before entering the cabinet 14.

Still referring to FIG. 2A, in some aspects, the air purifying duct system 24 may be positioned to circulate air between a refrigerator storage compartment and a freezer storage compartment. In some aspects, an evaporator (not shown) and a fan 30a may be positioned or located in the freezer compartment. The air purifying duct system 24, plenum, and/or multiflow may each be used to circulate air inside the freezer storage compartment and between the refrigerator and freezer storage compartments. In some aspects, the application of the photocatalyst 38 activated by the UV LEDs 42 is performed inside the air purifying duct system 24 that carry the air back and forth between the refrigerator and freezer storage compartments. In some aspects, the air circulation path 46 may be directed by the same fan 30a that circulates air through the evaporator to cool down the air using a single duct system for both air purification and air conditioning/cooling.

Figure 6A:
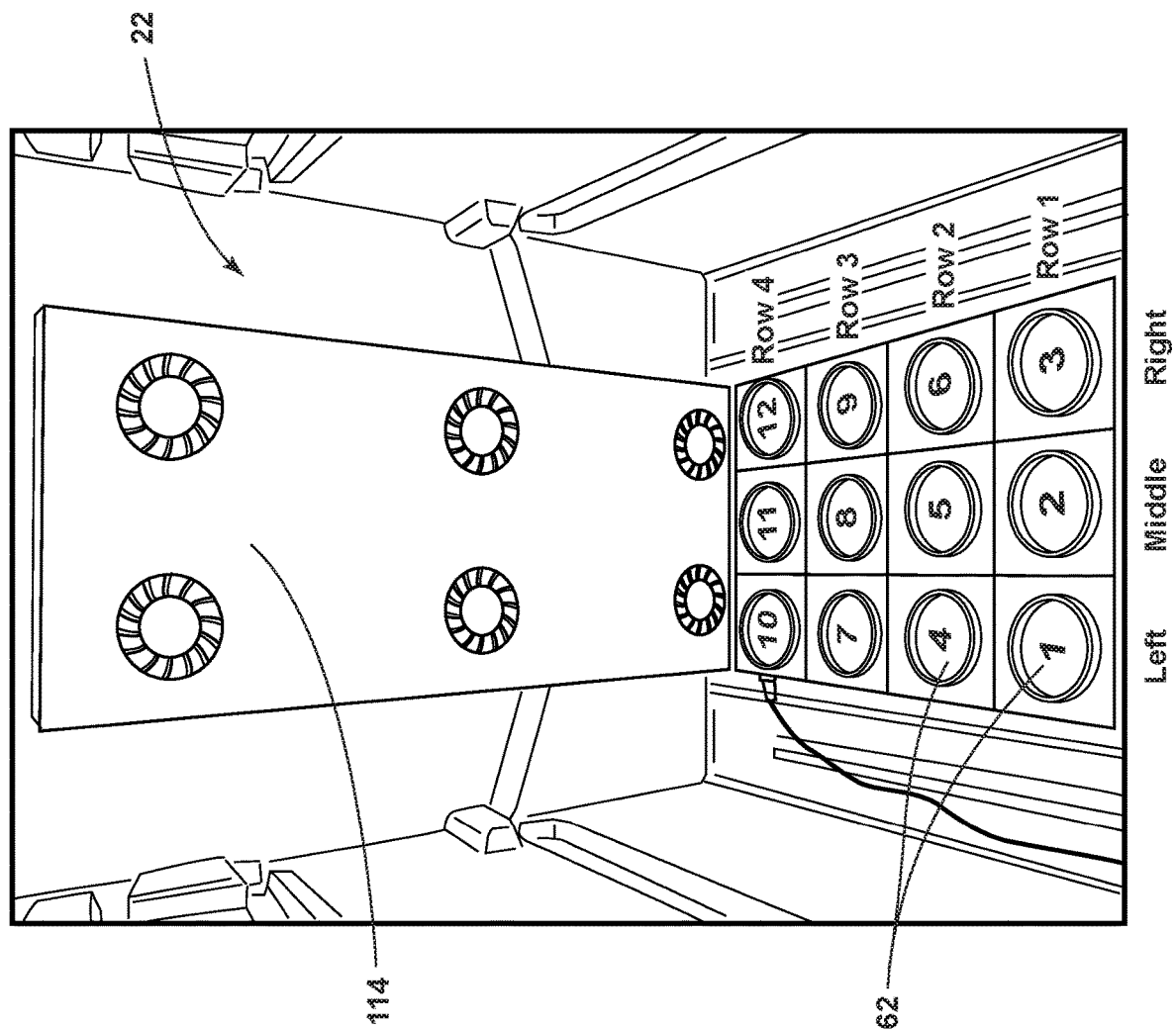
FIG. 6A is a picture of the experimental set up of the nebulization of an inoculum solution using a filter assembly for fan filtration according to some aspects of the present disclosure.
Figure 6B:
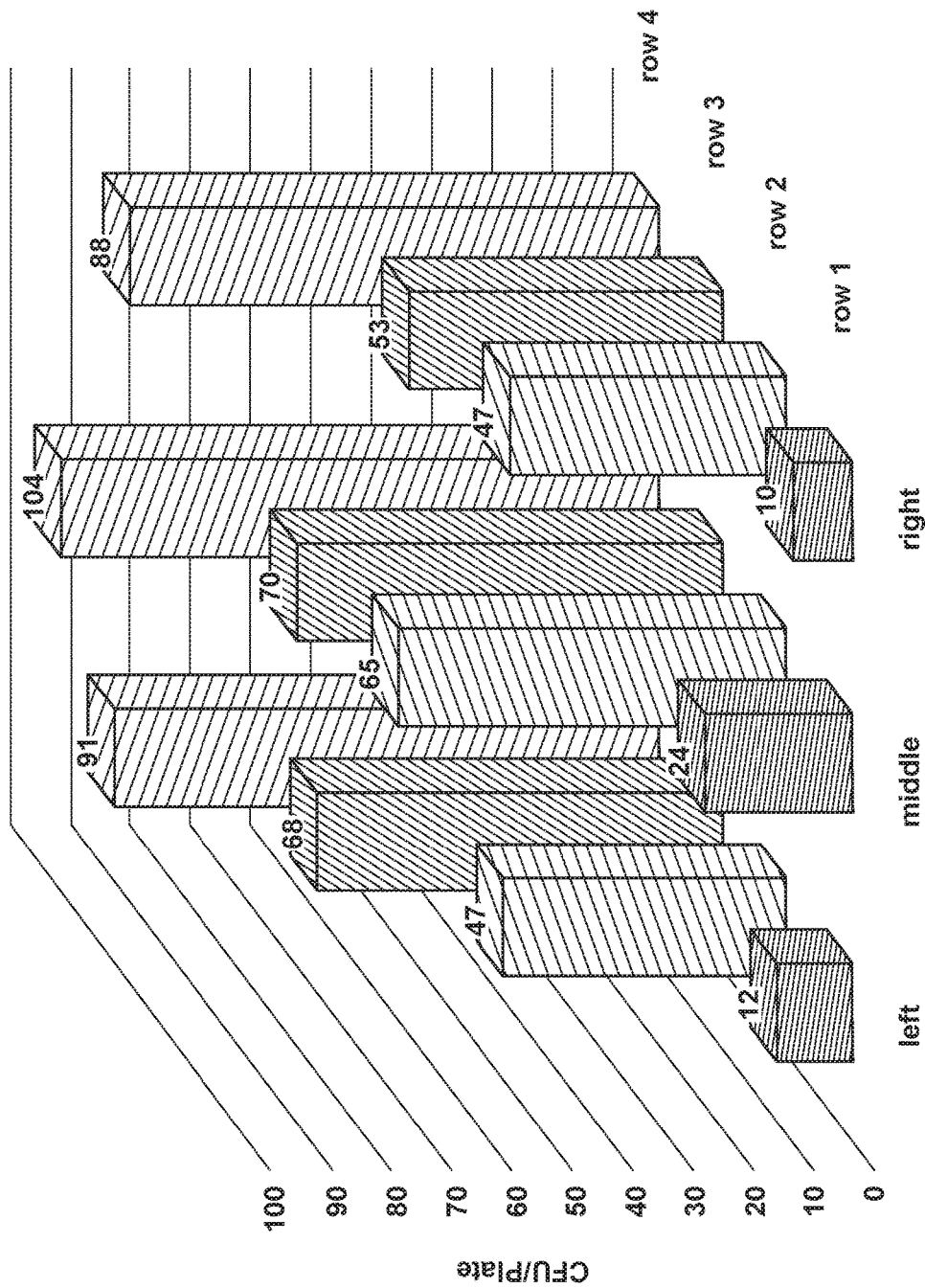
FIG. 6B is a distribution of microbial populations in a control using one filter assembly.
Figure 6C:
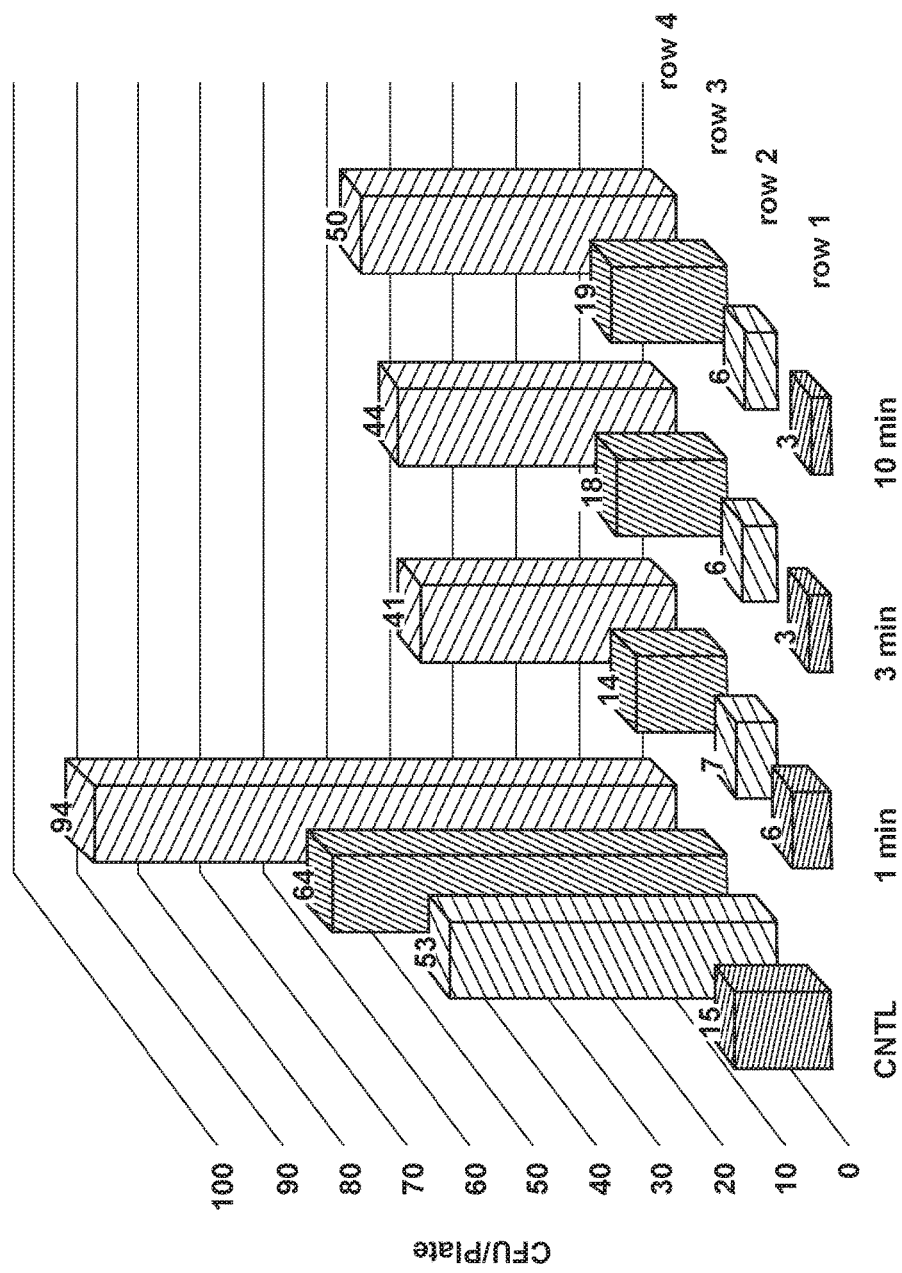
FIG. 6C provides averages of the distribution of microbial populations at various different times.

As will be provided in more detail in the description for FIGS. 6A-6C, the combination of two or more air duct intakes 66 are configured to provide the air circulation path 46 that directs the airborne bacteria 50, particulate matter 52, total solid particle (TSP), volatile organic compounds (VOCs), fungi, and/or molds simultaneously or contemporaneously into the air purifying duct system 24 using two or more circulation fans 30. The fans 30 direct the polluted air through the air duct 26 that may include the nano-coating 54 and/or the photocatalyst 38 irradiated by UV and/or visible light projected from the LEDs 42 to disinfect, filter, and/or clean the polluted air to circulate filtered air into the storage compartment 22 of the refrigerator 10. As provided in FIGS. 1C, 6B, and 6C, the use of just one air duct intake 66 may be unable to provide an air circulation path 46 that can effectively eliminate enough of the airborne bacteria 50. In some aspects, two or more air duct intakes 66 may be positioned on opposing first and second cabinet walls, positioned on the first and second doors 18a, 18b, or positioned on any two opposing interior surfaces where the two or more air duct intakes 66 work in a complementary manner to provide the improved air circulation path 46. The air circulation path 46 using two or more air duct intakes 66 may better direct the pathogens including airborne bacteria 50, particulate matter 52, TSP, volatile organic compounds (VOCs), fungi, and/or molds into the air purifying duct system 24 to be filtered.

In some aspects, the number of air duct intakes 66 and the number of air duct exhausts 74 may be limited to the number of circulation fans 30 incorporated into the air purifying duct system 24 based on the design and/or final air circulation properties desired for the refrigerator 10. In some aspects, the number of air duct intakes 66 may be two, three, four or more while the number of air duct exhausts 74 may include one, two, three, four, or more where the air duct intakes 66 and air duct exhausts 74 may be positioned with respect to each other in any combination. As illustrated in FIG. 2A, a main circulation fan 30a may be used in addition to or in place of the one or more fans 30 to provide the air circulation path 46.

Figure 2B:
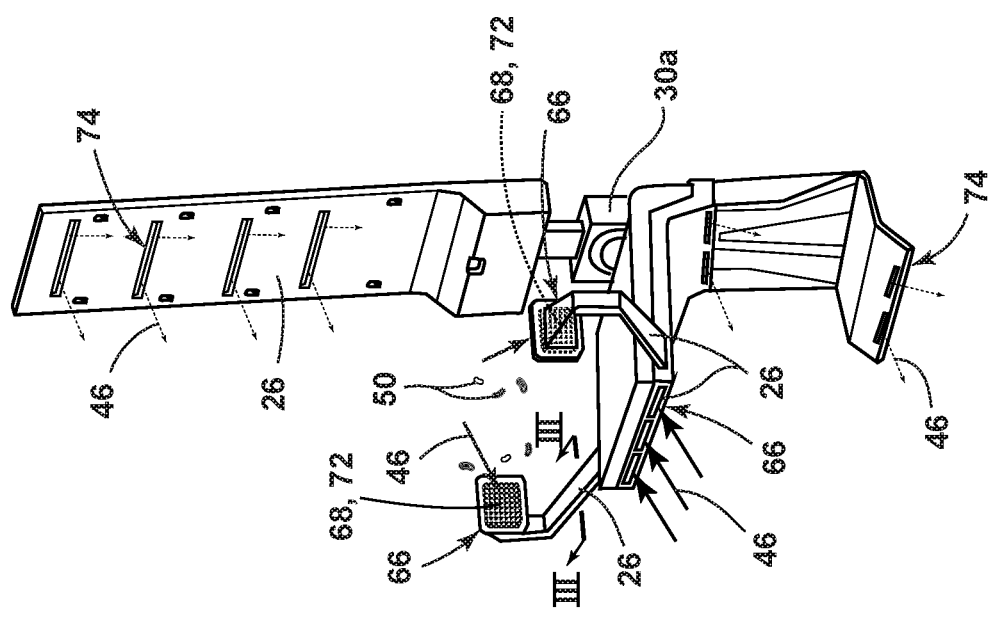
FIG. 2B is an isolated isometric view of an air purifying duct system according to some aspects of the disclosure.

Referring now to FIG. 2B, a partially schematic fragmentary view of the air purifying duct system 24 is provided. As illustrated, airborne bacteria 50 and/or particulate matter 52 scattered throughout the storage compartment 22 (see FIG. 1D) are directed along the air circulation path 46 into at least one of the air duct intakes 66 of the air purifying duct system 24. The air circulation path 46 generally flows between the area of the storage assembly 22 and the one or more air purifying duct systems 24 using one or more (e.g. two, three, four) circulation fans 30 positioned in each air purifying duct system 24. As provided in FIGS. 1B, 1C, and 1D, the air introduced into the storage compartment 22 when opening the refrigerator doors 18a, 18b (see FIG. 1D) can include airborne bacteria 50 and/or particulate matter 52. Once the refrigerator doors 18a, 18b and corresponding storage compartment 22 are closed, the air circulation path 46 generated by the one or more fans 30 direct the airborne bacteria 50 and/or particulate matter 52 in through air duct intake 66 to pass through the air duct 26 and out through the air duct exhaust 74. Any combination of interior surfaces 34 of the one or more air ducts 26, one or more fans 30, one or more air duct intakes 66, and/or one or more air duct exhausts 74 may be coupled to the photocatalyst 38 and/or nano-coating 54. As the airborne bacteria 50 and/or particulate matter 52 contact the photocatalyst 38, one or more LEDs 42 (see FIG. 3A) can project UV and/or visible light onto the photocatalysts 38 coupled to the interior surface 34 of the air ducts 26, fans 30, air duct intakes 66, and/or air duct exhausts 74. The photocatalyst 38 may be activated by the UV LED light, where the activated photocatalyst 38 can then kill and/or damage the airborne bacteria 50. The dead or damaged airborne bacteria 50 and/or particulate matter 52 may be circulated back into the storage compartment 22 in aspects where no filter is coupled to the air purifying duct system 24. The corresponding or resultant outlet purified air continues along the air circulation path 46 out through the air duct exhaust 74 and back into the storage compartment 22 of the cabinet 14.

In some aspects, a filter 72 may be coupled and/or positioned in the air circulation path 46 to help remove the dead or damaged airborne bacteria 50 and/or particulate matter 70 from being circulated back into the storage compartment 22 of the cabinet 14. In some aspects, the filter 72 or filter membrane may be made from a polymer fiber, a glass fiber, a ceramic fiber, or a combination thereof. The polymer fiber may include polyethylene (PE), polypropylene (PP), polyester, polyamide, polyvinylpolypyrrolidone (PVPP), polystyrene, polyimides, naturally occurring polymers, thermoplastics, thermosets, or combinations thereof. In some aspects, the polymer fiber used to make the filter 72 is polyethylene, polypropylene, a blend of polyethylene, and/or a blend of polypropylene.

The air purifying duct system 24 is able to purify the air and reduce pathogens when: 1) the doors 18 coupled to the refrigerator 10 are opened and closed to introduce new pathogens and particulate matter into the storage compartment 22; and/or 2) contaminated foodstuffs including meats and product release or introduce new pathogens and particulate matter into the storage compartment 22. In some aspects, the air purifying duct system 24 can completely circulate the entire volume of air in the storage compartment 2 to 50 times in a 24-hour period, 2 to 25 times in a 24-hour period, 2 to 15 times in a 24-hour period, or 3 to 5 times in a 24-hour period.

Figure 3A:
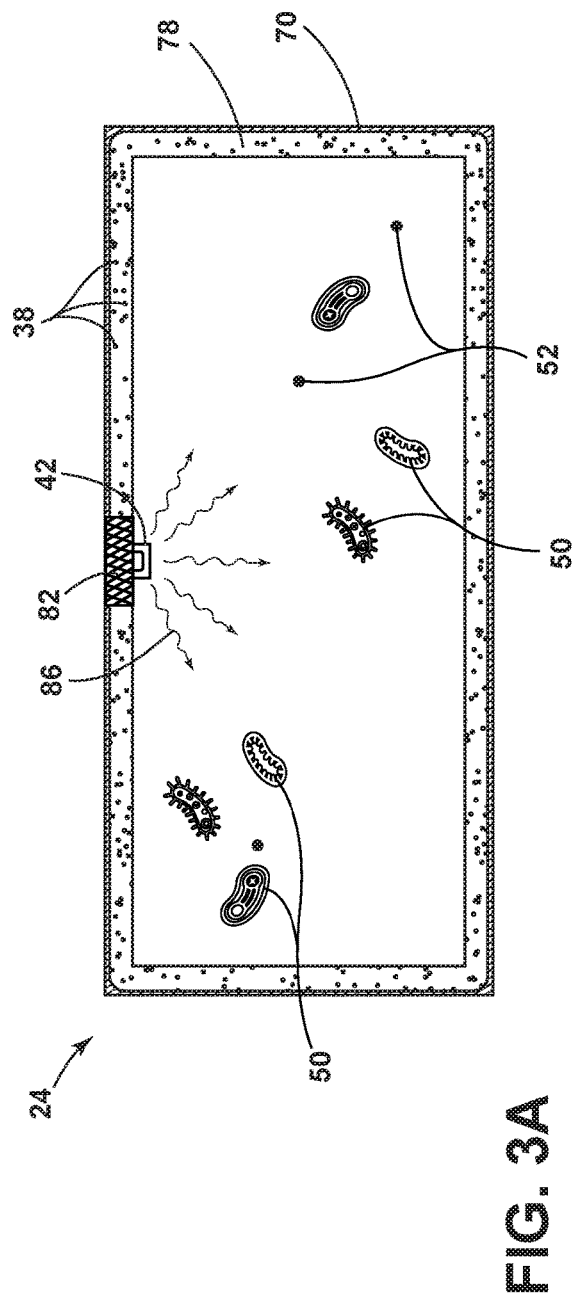
FIG. 3A is a cross-sectional view of the air purifying duct assembly incorporating a photocatalyst taken along the line III-III in FIG. 2A.

Referring now to FIG. 3A, a cross-sectional view of the air purifying duct system 24 taken along the line III-III in FIG. 2A is provided according to some aspects of the present disclosure. The air duct 26 includes at least one duct wall 70 where the duct wall 70 may have any design or shape known by one skilled in the art. The duct wall 70 may be coupled to a coating 78 including the photocatalyst 38. An LED panel 82 may be operatively coupled to a portion of one or more of the duct walls 70 enabling the one or more LEDs 42 to project light onto the photocatalyst 38. The light-activated photocatalyst 38 and/or light 86 produced from the LEDs 42 may interact with the deoxyribonucleic acid (DNA) and/or trigger a cascade of other biological reactions in harmful bacteria 50 responsible for the spoilage of food stored at low temperatures in refrigerators.

In some aspects, the photocatalyst 38 may include a UV and/or visible light activated photocatalyst including, but not limited to, titanium dioxide ($TiO_2$), zirconium dioxide ($ZrO_2$), silver (Ag), gallium (Ga), zinc oxide (ZnO), tin oxide ($SnO_2$), cesium oxide ($CeO_2$), zinc titanium dioxide ($ZnTiO_2$), copper titanium dioxide ($CuTiO_2$), silver titanium dioxide ($AgTiO_2$), iron titanium dioxide ($FeTiO_2$), or combinations thereof. In some aspects, the titanium dioxide ($TiO_2$), zirconium dioxide ($ZrO_2$), silver (Ag), gallium (Ga), zinc oxide (ZnO), tin oxide ($SnO_2$), cesium oxide ($CeO_2$), zinc titanium dioxide ($ZnTiO_2$), copper titanium dioxide ($CuTiO_2$), silver titanium dioxide ($AgTiO_2$), iron titanium dioxide ($FeTiO_2$), or combinations thereof used for the photocatalyst 38 may each be applied and/or used as nanoparticles. In some aspects, the photocatalyst's 38 titanium dioxide ($TiO_2$) nanoparticles, zirconium dioxide ($ZrO_2$) nanoparticles, silver (Ag) nanoparticles, gallium (Ga) nanoparticles, zinc oxide (ZnO) nanoparticles, tin oxide ($SnO_2$) nanoparticles, cesium oxide ($CeO_2$) nanoparticles, zinc titanium dioxide ($ZnTiO_2$) nanoparticles, copper titanium dioxide ($CuTiO_2$) nanoparticles, silver titanium dioxide ($AgTiO_2$) nanoparticles, iron titanium dioxide ($FeTiO_2$) nanoparticles, or combinations thereof may have a size from about 1 nm to about 100 nm, from about 1 nm to about 25 nm, from about 50 nm to about 100 nm, or from about 25 nm to about 75 nm. In some aspects, the photocatalyst 38 includes titanium dioxide ($TiO_2$). In other aspects, the photocatalyst 38 may include a mixture of titanium dioxide ($TiO_2$) and silver (Ag) or a mixture of zirconium dioxide ($ZrO_2$) and gallium (Ga). In still other aspects, the photocatalyst 38 may include a mixture of titanium dioxide ($TiO_2$), silver (Ag), zirconium dioxide ($ZrO_2$), and/or gallium (Ga). The photocatalyst 38 may be coated, coupled, and/or adsorbed onto the interior surface 34 of the air ducts 26, fans 30, air duct intakes 66, and/or air duct exhausts 74 using a variety of techniques including, for example, a sol gel approach. In some aspects, the interior surface 34 of the duct wall 70, air ducts 26, fans 30, air duct intakes 66, and/or air duct exhausts 74 includes a polyethylene material having a photocatalytic titanium dioxide ($TiO_2$) film deposited on its surface forming a nanostructured $TiO_2$ layer using sol gel. In other aspects, the interior surface 34 of the duct wall 70, air ducts 26, fans 30, air duct intakes 66, and/or air duct exhausts 74 may further or alternatively include an activated carbon and/or carbon black particles used to help filter polluted air circulated through the air purifying duct system 24. The $TiO_2$ or other photocatalyst 38 doped sol gel may include any sol gel or sol gel technique or method known in the art. The photocatalyst 38 may be operatively coupled to the interior surface 34 of the duct wall 70, air ducts 26, fans 30, air duct intakes 66, and/or air duct exhausts 74 using sol gel techniques or any other coating applications known by one skilled in the art (e.g., spin coating, solvent evaporation, spray coating, brushing, etc.).

Figure 3B:
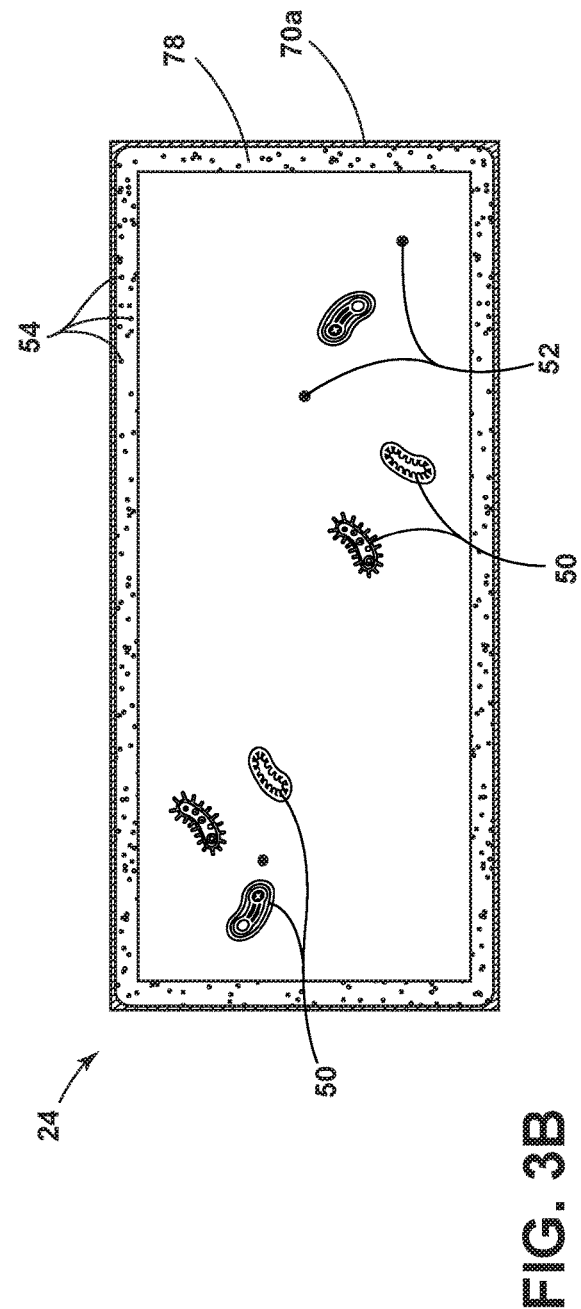
FIG. 3B is a cross-sectional view of the air purifying duct assembly incorporating a nano-coating taken along the line III-III in FIG. 2A.

Referring now to FIG. 3B, a cross-sectional view of the air purifying duct system 24 taken along the line III-III in FIG. 2A is provided according to other aspects of the present disclosure. The air duct 26 includes at least one duct wall 70 where the duct wall 70 may have any design or shape known by one skilled in the art. The duct wall 70 may be coupled to a coating 78a including the nano-coating 54. In aspects where the air purifying duct system 24 is coupled to the nano-coating 54, the use of one or more LEDs 42 to project light onto the nano-coating 54 is not required. The nano-coating 54 itself, or without any photoactivation or excitation, is able to interact with the airborne bacteria 50 to trigger cell death and/or a cascade of other biological reactions to help prevent bacterial spoilage of food stored at low temperatures in refrigerators.

In some aspects, the nano-coating 54 may include, but is not limited to, titanium dioxide ($TiO_2$), zirconium dioxide ($ZrO_2$), silver (Ag), gallium (Ga), zinc oxide (ZnO), tin oxide ($SnO_2$), cesium oxide ($CeO_2$), zinc titanium dioxide ($ZnTiO_2$), copper titanium dioxide ($CuTiO_2$), silver titanium dioxide ($AgTiO_2$), iron titanium dioxide ($FeTiO_2$), or combinations thereof. In some aspects, the nano-coating 54 includes a mixture of titanium dioxide ($TiO_2$), zirconium dioxide ($ZrO_2$), silver (Ag), and/or gallium (Ga). In some aspects, the titanium dioxide ($TiO_2$), zirconium dioxide ($ZrO_2$), silver (Ag), gallium (Ga), zinc oxide (ZnO), tin oxide ($SnO_2$), cesium oxide ($CeO_2$), zinc titanium dioxide ($ZnTiO_2$), copper titanium dioxide ($CuTiO_2$), silver titanium dioxide ($AgTiO_2$), iron titanium dioxide ($FeTiO_2$), or combinations thereof used for the nano-coating 54 may each be applied and/or used as nanoparticles. In some aspects, the nano-coating's 54 titanium dioxide ($TiO_2$) nanoparticles, zirconium dioxide ($ZrO_2$) nanoparticles, silver (Ag) nanoparticles, gallium (Ga) nanoparticles, zinc oxide (ZnO) nanoparticles, tin oxide ($SnO_2$) nanoparticles, cesium oxide ($CeO_2$) nanoparticles, zinc titanium dioxide ($ZnTiO_2$) nanoparticles, copper titanium dioxide ($CuTiO_2$) nanoparticles, silver titanium dioxide ($AgTiO_2$) nanoparticles, iron titanium dioxide ($FeTiO_2$) nanoparticles, or combinations thereof may each have a size from about 1 nm to about 100 nm, from about 1 nm to about 25 nm, from about 50 nm to about 100 nm, or from about 25 nm to about 75 nm. The nano-coating 54 may be coated, coupled, and/or adsorbed onto the interior surface 34 of the air ducts 26, fans 30, air duct intakes 66, and/or air duct exhausts 74 using a variety of techniques including, for example, a sol gel approach. In some aspects, the interior surface 34 of the duct wall 70, air ducts 26, fans 30, air duct intakes 66, and/or air duct exhausts 74 includes a polyethylene material having a nano-coating 54 film deposited on its surface forming a nanostructured layer using sol gel. In other aspects, the interior surface 34 of the duct wall 70, air ducts 26, fans 30, air duct intakes 66, and/or air duct exhausts 74 may include an activated carbon and/or carbon black particles used to help filter polluted air circulated through the air purifying duct system 24. The nano-coating 54 applied using a doped sol gel may include any sol gel or sol gel technique or method known in the art. The nano-coating 54 may be operatively coupled to the interior surface 34 of the duct wall 70, air ducts 26, fans 30, air duct intakes 66, and/or air duct exhausts 74 using sol gel techniques or any other coating applications known by one skilled in the art (e.g., spin coating, solvent evaporation, spray coating, brushing, etc.). In some aspects, the nano-coating 54 may include a mixture of titanium dioxide ($TiO_2$) and silver (Ag). In other aspects, the nano-coating 54 may include a mixture of zirconium dioxide ($ZrO_2$) and gallium (Ga). In still other aspects, the nano-coating 54 may include a mixture of titanium dioxide ($TiO_2$), silver (Ag), zirconium dioxide ($ZrO_2$), and/or gallium (Ga).

In some aspects, the air purifying duct system 24 is able to provide at least a 50% microbial reduction in one minute, at least a 50% microbial reduction in three minutes, or at least a 50% microbial reduction in ten minutes. In other aspects, the air purifying duct system 24 is able to provide at least a 60% microbial reduction in one minute, at least a 60% microbial reduction in three minutes, or at least a 60% microbial reduction in ten minutes. In still other aspects, the air purifying duct system 24 is able to provide at least a 70% microbial reduction in one minute, at least a 70% microbial reduction in three minutes, or at least a 70% microbial reduction in ten minutes. In other aspects, the air purifying duct system 24 is able to provide at least an 80% microbial reduction in one minute, at least an 80% microbial reduction in three minutes, or at least an 80% microbial reduction in ten minutes.

In some aspects, the air purifying duct system 24 is able may be able to reduce the VOCs in the storage compartment 22 of the refrigerator 10 by up to about 10%, about 15%, about 20%, or about 25% in less than 40 minutes, less than 60 minutes, less than 80 minutes, less than 100 minutes, or less than 120 minutes. In some aspects, the air purifying duct system 24 with a filter incorporated may be able to reduce the Total Solid Particulate (TSP) in the storage compartment 22 of the refrigerator 10 by up to about 10%, about 15%, about 20%, about 25%, about 30%, about 35%, about 40%, or about 45%, in at least 40 minutes, at least 60 minutes, at least 80 minutes, at least 100 minutes, or at least 120 minutes.

Figure 4:
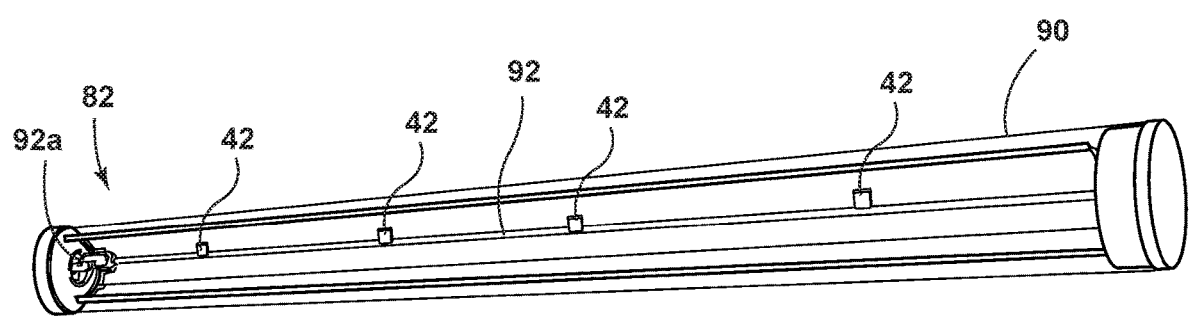
FIG. 4 is a front isometric view of a LED panel according to some aspects of the present disclosure.

Referring now to FIG. 4, a front isometric view of the LED panel 82 is provided. The LED panel 82 includes one or more LEDs 42 positioned along the length of the LED panel 82 in a linear, zig-zagged, or any other spaced pattern. The one or more LEDs 58 may project visible light, UV-A light, UV-B light, UV-C light, or a combination thereof onto the photocatalyst 38. The LED panel 82 may be simplified by welding the device wiring 92 to LED conductive tracks 92a of the LED panel 82 and the circulation fans 46. Construction and wiring in this manner allows the assembled air purifying duct system 24 to be achieved using only six tin solders. In some aspects, one or more LED panels 82 may include LEDs 42 that emit UV light and/or visible light. For example, in some aspects, the air purifying duct system 24 may include one LED panel 82 having white light LEDS for ambient lighting in the refrigerator 10 and a second LED panel (not shown) having UV LEDs used to activate the photocatalyst 38 coupled to the interior surface 34 of the air ducts 26, fans 30, air duct intakes 66, and/or air duct exhausts 74. The number of LED panels 82 and/or corresponding LEDs (both UV and other wavelengths) are not meant to be limiting and may be varied depending on the final design and corresponding functionality of the air purifying duct system 24 of the refrigerator 10.

Still referring to FIG. 4, the LEDs 42 mounted on the LED panel 82 may be positioned or spaced apart from the photocatalyst 38 by from about 0.5 cm to about 4 cm or from about 1 cm to about 3 cm. In some aspects, the LEDs 42 may be spaced apart from the photocatalyst 38 by about 0.5 cm, about 1 cm, about 1.5 cm, about 2 cm, about 2.5 cm, about 3 cm, about 3.5 cm, or about 4 cm. In some aspects, the LED panel 82 and corresponding LEDs 42 may be mounted or positioned directly in front of or across from the duct wall 70 coupled to the photocatalyst 38. In some aspects, the LEDs 42 generate UV light that can kill bacteria without the use of the photocatalyst 38. In other aspects, the photocatalyst 38 is activated when exposed to UV and/or visible light generated and projected by the LEDs 42 where the activated photocatalyst 38 may be able to kill and/or damage the bacteria. In some aspects, the LEDs 42 can project a wavelength from about 100 nm to about 405 nm, from about 250 nm to about 405 nm, or from about 395 nm to about 405 nm. In some aspects, the plurality of LEDs 42 are UV-A LEDs that are positioned to project UV-A light on the photocatalyst 38 coupled to the interior surface 34 of the duct wall 70, air ducts 26, fans 30, air duct intakes 66, and/or air duct exhausts 74. In other aspects, the plurality of LEDs 42 are UV-B LEDs that are positioned to project UV-B light on the photocatalyst 38 coupled to the interior surface 34 of the duct wall 70, air ducts 26, fans 30, air duct intakes 66, and/or air duct exhausts 74. In still other aspects, the plurality of LEDs 42 are UV-C LEDs that are positioned to project UV-C light on the photocatalyst 38 coupled to the interior surface 34 of the duct wall 70, air ducts 26, fans 30, air duct intakes 66, and/or air duct exhausts 74. In some aspects, the plurality of LEDs 42 are positioned to project UV-A light (315 nm to 400 nm), UV-B light (280 nm to 315 nm), UV-C light (100 nm to 280 nm), or a combination thereof on the photocatalyst 38 coupled to the interior surface 34 of the duct wall 70, air ducts 26, fans 30, air duct intakes 66, and/or air duct exhausts 74. In some aspects, the plurality of LEDs 42 are positioned to project UV-A light (315 nm to 400 nm) and UV-C light (100 nm to 280 nm) on the photocatalyst 38 coupled to the interior surface 34 of the duct wall 70, air ducts 26, fans 30, air duct intakes 66, and/or air duct exhausts 74. In other aspects, the LEDs 42 may project UV-A, UV-B, UV-C, or a combination of light thereof and/or visible light in the range from about 400 nm to about 700 nm. In still other aspects, the LEDs 42 may project visible light in the range from about 400 nm to about 700 nm.

Figure 5A:
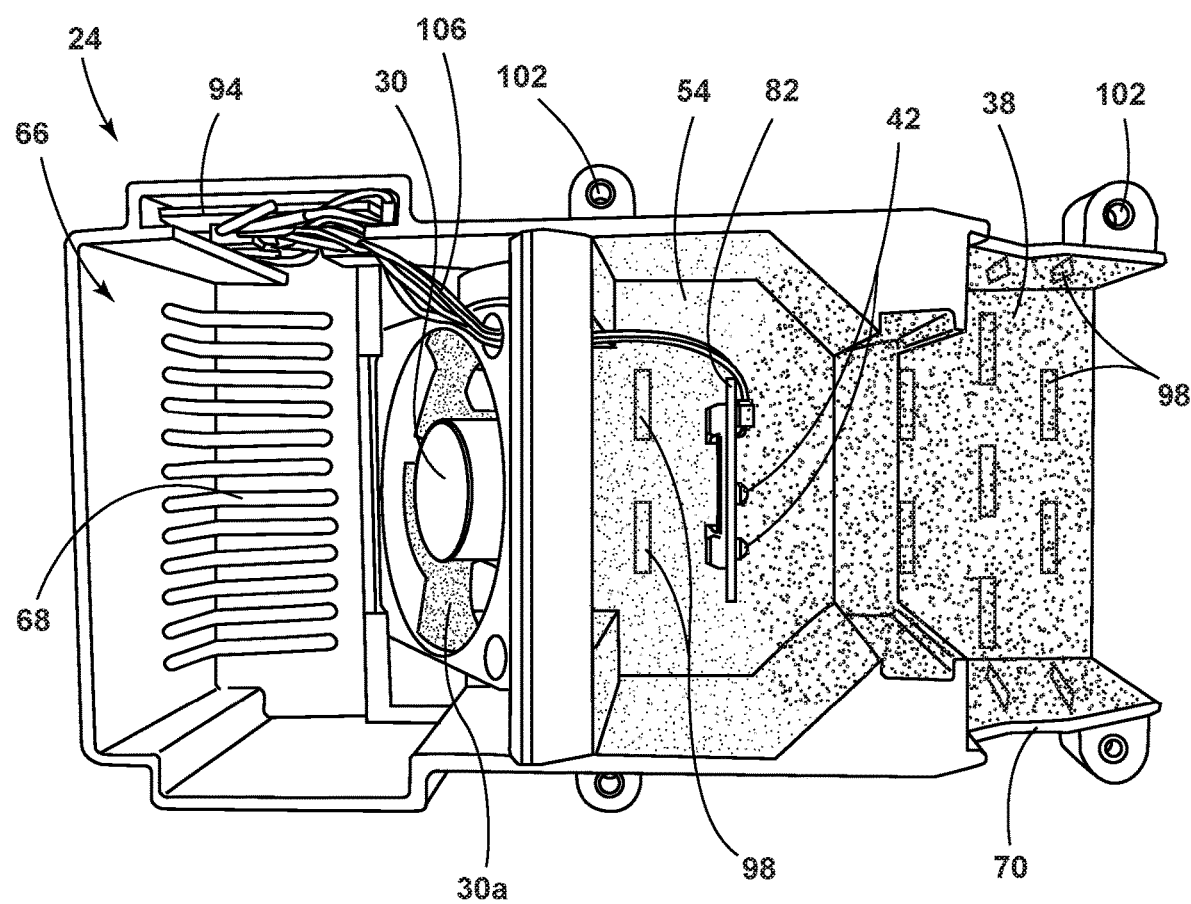
FIG. 5A is a top view of the air purifying duct system according to some aspects of the present disclosure.
Figure 5B:
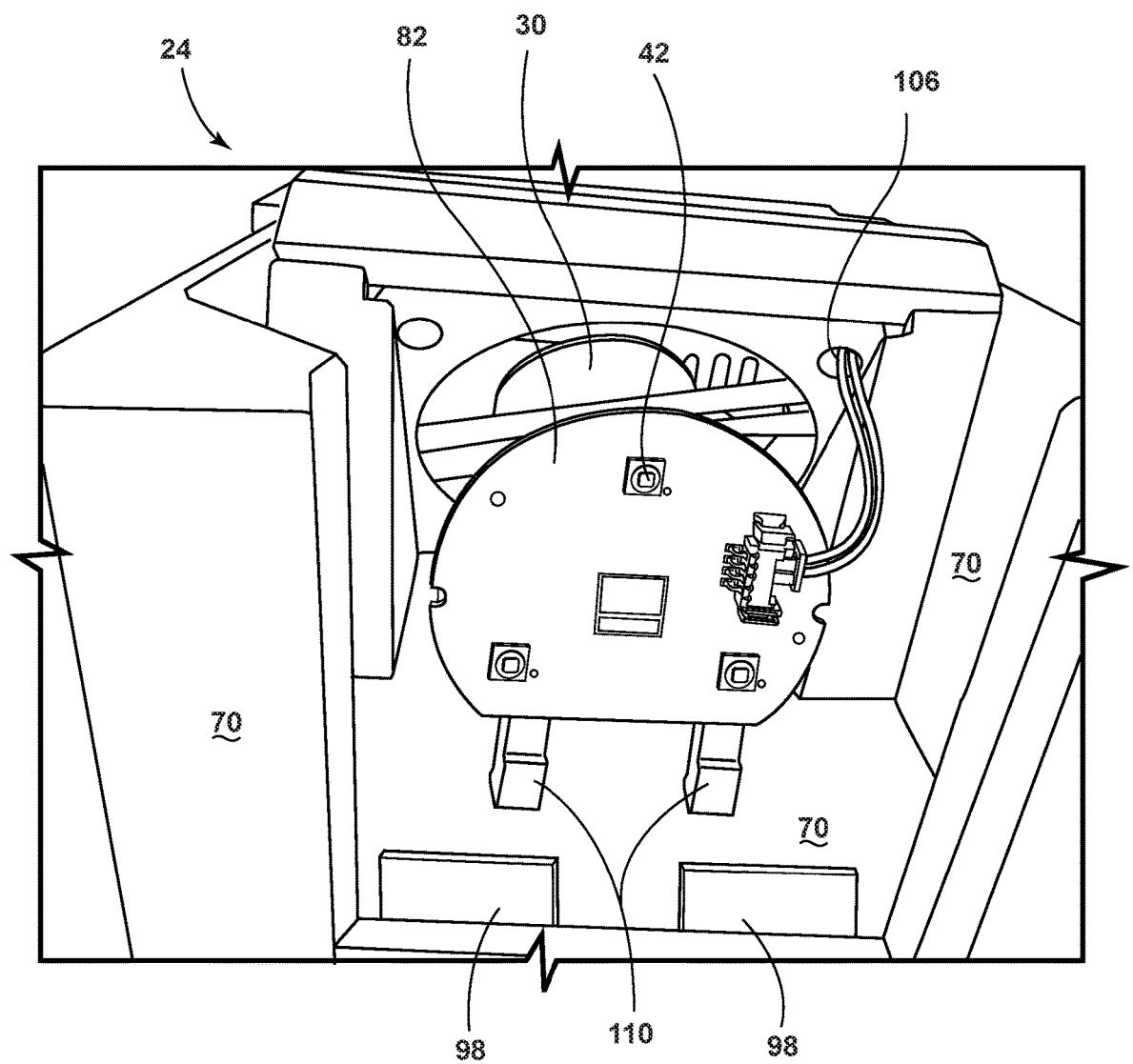
FIG. 5B is a side view of the air purifying duct system according to some aspects of the present disclosure.
Figure 5C:
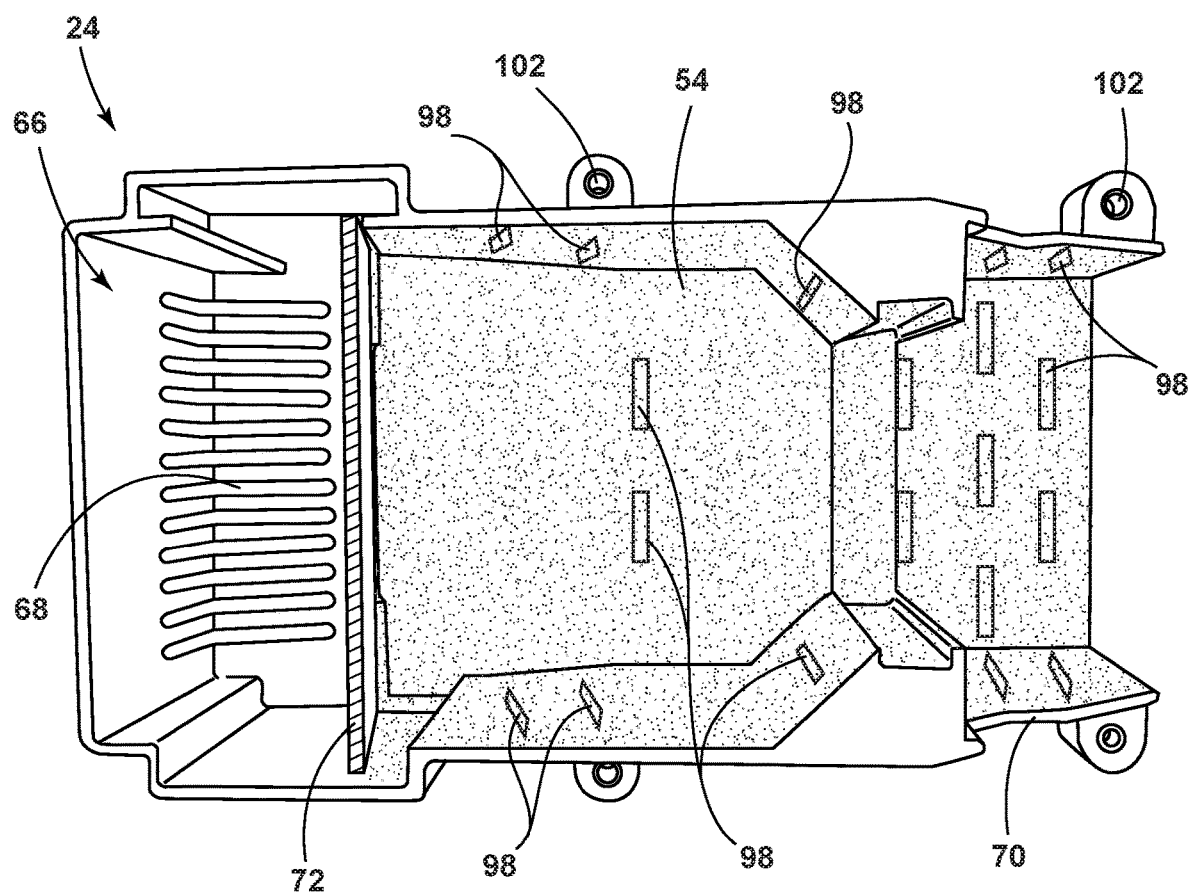
FIG. 5C is a top view of the air purifying duct system having a nano-coating according to some aspects of the present disclosure.

Referring now to FIGS. 5A-5C, a top view of the air purifying duct system 24 is provided according to some aspects of the present disclosure. The air purifying duct system 24 may include the fan 30 used to circulated polluted air in through the air duct intake 66 past the grate 68 and into the air duct 26. In some aspects, the photocatalyst 38 may be coupled to the interior surface 34 of the air ducts 26, fans 30, fan blades 30a, air duct intakes 66, and/or air duct exhausts 74. As illustrated in FIG. 5C, the nano-coating 54 may be coupled to the interior surface 34 of the air ducts 26, fans 30, air duct intakes 66, and/or air duct exhausts 74. Additionally illustrated in FIG. 5C, in some aspects, the air purifying duct system 24 does not include the fan 30 but rather one or more filters 72 positioned in the air duct 26 but may rather rely on fan 30a (see FIG. 2A) used to circulate cooled air from the evaporator used in the cooling cycle. As illustrated in FIG. 5A, in still other aspects, the photocatalyst 38 and nano-coating 54 may be selectively coated on any combination of air ducts 26, fans 30, air duct intakes 66, and/or air duct exhausts 74. In some aspects, one or more fins 98 may be positioned and coupled on the interior surface 34 of the duct wall 70 in the air duct 26 to help manipulate or control the air circulation path 46 passing through the air purifying duct system 24. In some aspects, the plurality of fins 98 may be coated with the photocatalyst 38 and/or the nano-coating 54. The LED panel 82 includes one or more LEDS 42 positioned to direct UV and/or visible light onto the coating 78 of photocatalyst 38. One or more attachment members 102 may be molded or attached to the air duct 26 to couple the air purifying duct system 24 to the cabinet 14 of the refrigerator 10. Coupling members (not shown) used to couple the attachment members 102 to the cabinet 14 may include for example, but are not limited to, screws, bolts, nails, clips, snaps, and/or ties. Wiring 106 may be used to couple the LED panel to a controller 94. In some aspects, the controller 94 drives and communicates with the one or more circulation fans 30 and LED's 42 as triggered by a pre-programmed schedule or program, the opening and closing of the refrigerator doors 18, the detection of odor, bacteria 50, and/or particulate matter 52 using, for example, a bio-sensor, and/or other triggers or factors known by one skilled in the art. FIG. 5B provides a side view of the air purifying duct system 24 where the LED panel 82 may be coupled to the air duct 26 using one or more duct mounting members 110. The LED panel 82 illustrated in FIGS. 5A-5C is projected down the length of the air duct 26 but in some aspects (see FIGS. 3A and 3B) the LED panel 82 may be positioned directly across one or more duct walls 70 to project selected wavelengths from the LEDs 42.

According to another aspect of the present disclosure, the refrigerator 10 is provided. The refrigerator 10 includes the cabinet 14 coupled to one or more doors 18 forming the storage compartment 22; the air duct 26 in fluid communication with the storage compartment 22; the fan 30 coupled to the interior surface 34 of the air duct 26 wherein the fan 30 is configured to circulate air between the storage compartment 22 and air duct 26; the nano-coating 54 disposed on a portion of the interior surface 34; and the air circulation path 46 configured to direct airborne bacteria 50 within the storage compartment 22 into the air duct 26 using the fan 30 and circulate purified air into the storage compartment 22.

It is understood that the descriptions outlining and teaching the refrigerator 10 having the photocatalyst 38 previously discussed, which can be used in any combination, apply equally well to the refrigerator 10 including the nano-coating 54 described herein.

According to still another aspect of the present disclosure, the air purifying duct system 24 is provided. The air purifying duct system 24 includes the air duct 26 in fluid communication with the storage compartment 22; the fan 30 coupled to the interior surface 34 of the air duct 26 wherein the fan 30 is configured to circulate air between the storage compartment 22 and air duct 26; the nano-coating 54 including a mixture of titanium dioxide ($TiO_2$) and silver (Ag), a mixture of zirconium oxide ($ZrO_2$) and gallium (Ga), or a mixture of titanium dioxide ($TiO_2$), silver (Ag), zirconium oxide ($ZrO_2$), and gallium (Ga); and the air circulation path 46 configured to direct airborne bacteria 50 within the storage compartment 22 into the air duct 26 using the fan 30 and circulate purified air into the storage compartment 22. In some aspects, the photocatalyst 38 may be used to replace or in addition to the nano-coating 54. In these aspects, the photocatalyst 38 may be disposed on a portion of the interior surface 34; one or more LEDs 42 positioned to project light across the air duct 26 and onto the photocatalyst 38

It is understood that the descriptions outlining and teaching several of the features included in the refrigerator 10 previously discussed, which can be used in any combination, apply equally well to the refrigerator 10 described herein having the photocatalyst 38 and/or the nano-coating 54.

EXAMPLES

The following examples and their corresponding data represent certain non-limiting examples of the air purifying duct system 24 used to effectively filter air in the storage compartment 22 of the refrigerator 10.

Materials

All chemicals, bacteria, growth media, and other constituents were obtained from commercial suppliers and used as provided. The examples herein provides a series of experiments performed according to the ASTM E 2315 and ISO 22196 international standards using minor modifications.

The antibacterial refrigerator 10 and its corresponding air purifying duct system 24 using the photocatalyst 38 with LEDs 42 and/or the nano-coating 54 are designed to remove and/or destroy contaminants such as odor, toxic particles, and pathogens. Examples of key substances that are typically removed through this air-treatment process include parasites, bacteria, algae, viruses, fungi, ethylene, and other food related chemical pollutants.

Air Circulation and Fan Positioning Examples

Referring now to FIGS. 6A-6C, a description of the experimental set up for the nebulization of an inoculum solution using the fan assemblies 26, 38 for air filtration in the storage compartment 22 is provided. The inoculum solution used in the experiments illustrated in FIG. 6A includes a microbial-loaded saline solution (50-70 ml) recovered during hand washing procedures. To quantify the overall microbial load of the test inoculum, the count of viable microorganisms was determined by means of the pour plate culture method. Briefly, the number of viable microorganisms was counted on Luria-Bertani broth (LB) agar petri dishes ($\theta$=60 mm) after serial ten-fold dilutions of the test inoculum suspensions and plating. Plating was performed in duplicate, and the number of viable microorganisms was determined according to the following equation: $N=(C \times D)/V$ where N=number of viable bacteria per ml; C=average plate count for the duplicate plates (e.g., number of colony forming units, CFU, determined in each LB-agar plate); D=dilution factor for the plate counted; and V=volume of test inoculum (in ml).

As illustrated in FIG. 6A, the inner compartment of a refrigerator (Whirlpool, BLFV8121W model) and the antibacterial device were first cleaned to remove any gross contamination using a quaternary benzyl ammonium disinfectant where the same cleaning procedure was performed on the storage compartment 22 in between each experiment. Following the cleaning procedure, the antibacterial device was placed inside the refrigerator and the refrigerator was left to equilibrate at 40° C. for at least 24 hours. Before nebulization of the inoculum solution was provided, 12 sterile LB-agar petri dishes 78 ($\theta$=60 ml, N=12) were placed inside the refrigerator compartment. The experiments included the nebulization of 450 microliters (4) of inoculum inside the refrigerator through a small hole made on the front wall of the refrigerator door ($\theta$=1.2 cm). Immediately upon the nebulization of the inoculum solution, a test air filtration device 114 was switched on and kept on for a variety of different time periods (e.g., 1 min, 3 min, 10 min) after a microbial nebulization. Control experiments were carried out in the same conditions, but the test air filtration device 114 was not activated. In each of the experiments, the LB-agar petri dishes 78 were closed about 10 minutes after the microbial nebulization and incubated for the first 24 hrs at 37° C., and then for an additional 48 hrs at room temperature (RT). The number of viable microorganisms was then counted on LB-agar petri dishes. All of the experiments noted were performed in triplicate. Data was normalized with respect to the number of viable counts and control samples (CTRL, e.g., air filtration device turned off), considering the number of microorganisms in such condition as 100%. Results are expressed as mean±standard deviation (SD).

Referring now to FIG. 6B, the distribution results of the microbial population measured in colony forming units (CFU) for the cultured control experiments are provided. A homogeneous distribution was found for each respective row, which seemed to be dependent on the distance from the nebulization inlet port and/or the test air filtration device 114. When the test air filtration device 114 was permitted to run for longer durations, the number of microorganisms decreased from about 50% eliminated to about 75% eliminated after one minute, and this decrease in CFU was maintained over time. This corresponding decrease was shown to be at least partly dependent on the distance from the test air filtration device 114. The row of LP-agar petri dishes 62 positioned closest to the test air filtration device 114 (Row 4) contained the highest microbial population relative to Rows 1-3 while lowest microbial population was observed in the row furthest from the test air filtration device 114 (Row 1). The uniform difference and disparity in microbial populations based on the difference in distance between the corresponding rows and the test filtration device 114 supports the need for the air purifying duct system 24 as described herein.

Referring now to FIG. 6C, the viable CFU counts for each of the four rows (Rows 1-4) were averaged and plotted against time as the test air filtration device 114 was operated to filter the storage compartment 22. Consistent with the data provided in FIG. 6B, when the filtration device was run for a longer period of time (e.g., 10 min vs. 3 min vs 1 min), the number of microorganisms decreased from about 50 to about 75% already after one minute and was generally maintained over the longer periods of time. Again consistent with the data provided in FIG. 6B, the decrease in CFU counted is dependent on the distance from the test air filtration device 114 where the decrease in CFU was more pronounced or greater at distances further away from the test air filtration device 114.

It will be understood by one having ordinary skill in the art that construction of the described device and other components may not be limited to any specific material. Other exemplary aspects of the device disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It will be understood that any described processes or steps within described processes may be combined with other disclosed processes or steps to form structures within the scope of the present device. The exemplary structures and processes disclosed herein are for illustrative purposes and are not to be construed as limiting.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It is also to be understood that variations and modifications can be made on the aforementioned structure without departing from the concepts of the present invention, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A refrigerator comprising:
    a cabinet coupled to one or more doors forming a storage compartment; and
    an air purifying duct system positioned in the storage compartment, wherein the air purifying duct system comprises:
        an air duct in fluid communication with the storage compartment, wherein the air duct includes at least two air duct intakes positioned on opposing sidewalls of the storage compartment and at least one air duct exhaust, wherein the at least two air duct intakes are fluidly coupled via the air duct;
        a fan configured to draw air from the storage compartment into the air duct through the at least two air duct intakes and exhaust the air into the storage compartment through the at least one air duct exhaust;
        a photocatalyst disposed on at least a portion of an interior surface of the air duct between the at least two air duct intakes and the at least one air duct exhaust;
        one or more LEDs positioned to project light onto the photocatalyst; and
        a controller operably coupled with the fan and the one or more LEDs; and
    wherein air that enters the at least two air duct intakes passes through the portion of the air duct containing the photocatalyst prior to exiting the air duct through the at least one air duct exhaust, further wherein upon detection of the one or more doors closing, the controller drives the fan to form an air circulation path configured to direct pathogens within the storage compartment into the air duct using the fan and the controller communicates with the one or more LEDs to emit light.

2. The refrigerator according to claim 1, wherein the one or more LEDs project visible light, UV-A light, UV-B light, UV-C light, or a combination thereof onto the photocatalyst.

3. The refrigerator according to claim 1, wherein the photocatalyst is a coating containing a mixture of titanium dioxide nanoparticles ($TiO_2$) and silver nanoparticles (Ag).

4. The refrigerator according to claim 1, wherein the photocatalyst is a coating containing a mixture of zirconium dioxide nanoparticles ($ZrO_2$) and gallium nanoparticles (Ga).

5. The refrigerator according to claim 1, wherein the photocatalyst comprises at least one material selected from titanium dioxide nanoparticles ($TiO_2$), zirconium dioxide nanoparticles ($ZrO_2$), silver nanoparticles (Ag), and gallium nanoparticles (Ga).

6. The refrigerator according to claim 1, wherein the air duct comprises a plurality of air duct exhausts positioned along a back wall of the storage compartment.

7. The refrigerator according to claim 1, wherein the air duct comprises a plurality of fins coated with the photocatalyst.

8. The refrigerator according to claim 1, wherein the photocatalyst is adapted to reduce airborne bacteria in the storage compartment by at least 60% within one minute.

9. The refrigerator according to claim 1, wherein the fan comprises one or more blades, and wherein the photocatalyst is additionally disposed on the one or more blades of the fan.

10. The refrigerator according to claim 1, further comprising a nano-coating disposed on at least a portion of the interior surface of the air duct.

11. The refrigerator according to claim 10, wherein the one or more LEDs are positioned to project light onto the at least a portion of the interior surface of the air duct containing the photocatalyst.

12. The refrigerator according to claim 1, wherein the air duct comprises:
    at least one filter disposed in the air circulation path between the at least two air duct intakes and the at least one air duct exhaust; and
    wherein the fan is configured to draw air into the air duct through the at least two air duct intakes and through the at least one filter before exhausting the air through the at least one air duct exhaust.

13. The refrigerator according to claim 1, wherein the storage compartment further comprises:
    a refrigerator storage compartment; and
    a freezer storage compartment, wherein the air purifying duct system circulates air between the refrigerator storage compartment and the freezer storage compartment.

14. A refrigerator comprising:
a cabinet coupled to one or more doors forming a storage compartment; and
an air purifying duct system positioned in the storage compartment, wherein the air purifying duct system comprises:
  at least one air duct in fluid communication with the storage compartment, wherein the at least one air duct includes an air duct intake and an air duct exhaust;
  a fan configured to draw air from the storage compartment into the at least one air duct through the air duct intake, wherein the air is circulated past an evaporator and into the storage compartment through the air duct exhaust;
  a photocatalyst disposed on at least one of the air duct intake and the air duct exhaust and further on at least a portion of the duct wall between the air duct intake and the air duct exhaust;
  one or more LEDs positioned to project light onto the photocatalyst;
  a controller operably coupled with the fan and the one or more LEDs; and
  wherein the fan is configured to draw air from the storage compartment and through the at least one air duct containing the photocatalyst, further wherein upon detection of the one or more doors closing, the controller drives the fan to form an air circulation path configured to direct pathogens within the storage compartment into the at least one air duct using the fan and the controller communicates with the one or more LEDs to emit light.

15. The refrigerator according to claim 14, wherein the storage compartment further comprises:
  a refrigerator storage compartment; and
  a freezer storage compartment, wherein the air purifying duct system circulates air between the refrigerator storage compartment and the freezer storage compartment.

16. A refrigerator comprising:
a cabinet coupled to one or more doors forming a storage compartment; and
an air purifying duct system positioned in the storage compartment, wherein the air purifying duct system comprises:
  at least one air duct in fluid communication with the storage compartment, wherein the at least one air duct includes an air duct intake and an air duct exhaust;
  a fan configured to draw air from the storage compartment into the at least one air duct through the air duct intake, wherein the air is circulated past an evaporator and into the storage compartment through the air duct exhaust;
  a plurality of fins disposed on at least a portion of a duct wall between the air duct intake and the air duct exhaust;
  a photocatalyst disposed on at least one of the air duct intake and the air duct exhaust and further on the plurality of fins and on at least a portion of the duct wall between the air duct intake and the air duct exhaust;
  one or more LEDs positioned to project light onto the photocatalyst; and
  a controller operably coupled with the fan and the one or more LEDs; and
  wherein the fan is configured to draw air from the storage compartment and through the at least one air duct containing the photocatalyst, further wherein upon detection of the one or more doors closing, the controller drives the fan to form an air circulation path configured to direct pathogens within the storage compartment into the at least one air duct using the fan and the controller communicates with the one or more LEDs to emit light.

17. The refrigerator according to claim 16, wherein the one or more LEDs project visible light, UV-A light, UV-B light, UV-C light, or a combination thereof onto the photocatalyst.

18. The refrigerator according to claim 16, wherein the photocatalyst is a coating containing a mixture of titanium dioxide nanoparticles ($TiO_2$) and silver nanoparticles (Ag).

19. The refrigerator according to claim 16, wherein the photocatalyst is a coating containing a mixture of zirconium dioxide nanoparticles ($ZrO_2$) and gallium nanoparticles (Ga).

20. The refrigerator according to claim 16, wherein the photocatalyst comprises at least one material selected from titanium dioxide nanoparticles ($TiO_2$), zirconium dioxide nanoparticles ($ZrO_2$), silver nanoparticles (Ag), and gallium nanoparticles (Ga).

21. The refrigerator according to claim 16, wherein the at least one air duct comprises first and second air ducts positioned on opposing sidewalls of the storage compartment.

22. The refrigerator according to claim 16, wherein the fan comprises one or more blades, and wherein the photocatalyst is additionally disposed on the one or more blades of the fan.

23. The refrigerator according to claim 16, wherein the storage compartment further comprises:
  a refrigerator storage compartment; and
  a freezer storage compartment, wherein the air purifying duct system circulates air between the refrigerator storage compartment and the freezer storage compartment.

* * * * *